US010744238B2

(12) United States Patent
Guidi et al.

(10) Patent No.: US 10,744,238 B2
(45) Date of Patent: Aug. 18, 2020

(54) DRAINAGE DEVICE PARTICULARLY FOR ASPIRATION IN CASE OF THERAPIES WITH ASPIRATION, FISTULAS, DEHISCENCES OF SURGICAL WOUNDS, BEDSORES, TRAUMAS AND SIMILAR LESIONS

(71) Applicant: NidiCare GmbH, Imst (AU)

(72) Inventors: Daniele Guidi, Corciano (IT); Alberto Guidi, Corciano (IT)

(73) Assignee: NIDICARE GMBH, Imst (AT)

( * ) Notice: Subject to any disclaimer, the term of this patent is extended or adjusted under 35 U.S.C. 154(b) by 325 days.

(21) Appl. No.: 15/286,793

(22) Filed: Oct. 6, 2016

(65) Prior Publication Data

US 2017/0087282 A1    Mar. 30, 2017

Related U.S. Application Data

(63) Continuation of application No. 12/680,832, filed as application No. PCT/EP2009/002686 on Apr. 9, 2009, now Pat. No. 10,624,999.

(30) Foreign Application Priority Data

May 26, 2008  (IT) .............................. AR2008A0022
Dec. 10, 2008  (WO) ................. PCT/EP2008/067241

(51) Int. Cl.
*A61M 1/00*   (2006.01)
*A61M 27/00*  (2006.01)
(Continued)

(52) U.S. Cl.
CPC ....... *A61M 1/0023* (2013.01); *A61F 13/0209* (2013.01); *A61F 13/0213* (2013.01); *A61F 13/0216* (2013.01); *A61M 1/0088* (2013.01); *A61M 27/00* (2013.01); *A61F 2013/00412* (2013.01)

(58) Field of Classification Search
CPC ...... A61F 13/02–0266; A61F 13/00068; A61F 2013/00412; A61M 1/0023; A61M 1/0088; A61M 27/00
See application file for complete search history.

(56) References Cited

U.S. PATENT DOCUMENTS

| 3,568,675 A | 3/1971 | Harvey |
| 5,549,584 A | 8/1996 | Gross |

(Continued)

FOREIGN PATENT DOCUMENTS

| CN | 101065158 A | 10/2007 |
| EP | 1 092 404 A1 | 4/2001 |

(Continued)

OTHER PUBLICATIONS

International Search Report for PCT/EP2009/002686, 4 pages.

*Primary Examiner* — Benjamin J Klein
(74) *Attorney, Agent, or Firm* — Fay Sharpe LLP (57) ABSTRACT

A drainage device (1) particularly for aspiration in case of therapies with aspiration, fistulas, dehiscences of surgical wounds, bedsores, traumas and similar lesions, comprising an aspiration pouch (2) which is supported by a sheet-like element (5) which can be associated with the lesion (10) and is connected to aspiration means (3) by way of a connecting element (4).

19 Claims, 10 Drawing Sheets

(51) Int. Cl.
*A61F 13/02* (2006.01)
*A61F 13/00* (2006.01)

(56) References Cited

U.S. PATENT DOCUMENTS

| | | | |
|---|---|---|---|
| 7,699,823 B2* | 4/2010 | Haggstrom | A61M 1/0031 604/305 |
| 7,880,050 B2 | 2/2011 | Robinson et al. | |
| 8,945,030 B2* | 2/2015 | Weston | A61M 1/0088 602/2 |
| 2001/0031943 A1* | 10/2001 | Urie | A61M 1/0088 604/43 |
| 2003/0212357 A1* | 11/2003 | Pace | A61F 13/0203 602/41 |
| 2005/0101940 A1 | 5/2005 | Radl et al. | |
| 2005/0137539 A1 | 6/2005 | Biggie et al. | |
| 2007/0282236 A1* | 12/2007 | LaGreca | A61F 13/0206 602/43 |
| 2008/0063695 A1 | 3/2008 | Vitaris | |
| 2008/0119802 A1* | 5/2008 | Riesinger | A61F 13/00068 604/313 |
| 2008/0306456 A1 | 12/2008 | Riesinger | |
| 2009/0227969 A1* | 9/2009 | Jaeb | A61M 1/0088 604/313 |
| 2010/0174250 A1 | 7/2010 | Hu et al. | |
| 2011/0152778 A1 | 6/2011 | Gyrn | |

FOREIGN PATENT DOCUMENTS

| | | |
|---|---|---|
| WO | 2000/07653 A1 | 2/2000 |
| WO | 2008/041926 A1 | 4/2008 |
| WO | 2009/021353 A1 | 2/2009 |

\* cited by examiner

DRAINAGE DEVICE PARTICULARLY FOR ASPIRATION IN CASE OF THERAPIES WITH ASPIRATION, FISTULAS, DEHISCENCES OF SURGICAL WOUNDS, BEDSORES, TRAUMAS AND SIMILAR LESIONS

CROSS-REFERENCE TO RELATED APPLICATIONS

This application is a continuation application of U.S. patent application Ser. No. 12/680,832, filed Mar. 30, 2010; which is national stage entry of International Application Number PCT/EP2009/002696, filed Apr. 9, 2009; and also claims the priority benefit of Italian application No. AR2008A000022, filed May 26, 2008 and German application No. PCT/EP2008/067241, filed Dec. 10, 2008. The contents of each of these four priority applications are incorporated by reference herein in their entireties.

TECHNICAL FIELD

The present invention relates to a drainage device particularly for aspiration in case of therapies with aspiration, fistulas, dehiscences of surgical wounds, bedsores, traumas and similar lesions, such as for example venous and arterial ulcers or lesions due to diabetic foot.

BACKGROUND ART

Devices of this type are known which comprise a film which covers at least one layer of polyurethane and a drainage tube, which is applied to the lesion and to which a connecting valve is connected which allows connection to aspiration means.

For medications inside the lesion and for performing occlusive medications, particularly if the lesions are of the cavitary type, the filling of the cavitary lesion with a first layer of polyurethane for the plug (application of polyurethane in contact with the lesion) is performed, followed by the application of an expanded polyurethane compress for drainage.

In a first type of known device, a drainage tube is inserted within the cavitary lesion and then such cavity is closed by applying an adhesive film.

Another type of device blocks the cavity with an adhesive film and by resting a flared connection, connected to the drainage tube, in contact with the polyurethane compress.

In any case, the tube is connected to the aspiration means, thus allowing to aspirate serum, exuded matter and liquids to be removed.

A device of this type has unwanted drawbacks and problems.

First of all, the application of the draining tube, which moreover in some cases can be unpleasant for the patient, is rather complicated and requires the intervention of qualified personnel.

Further, devices of this type are scarcely practical, since often it is necessary to limit contact between the film and the skin of the patient, which is particularly irritable and sensitive in the region affected by the lesion.

However, in such devices, when the liquids to be removed are aspirated, bleeding problems often arise due to the aspiration effect at the lips of the cavity. In addition to this, due to the irregular shape that these cavities have, the adhesion of the film to the skin is not perfect, and this leads to infiltrations of air in the drainage pouch, and therefore asepsis of the method and vacuum are not ensured.

Finally, in some circumstances, for example on lesions located in the region of the lower back or buttocks, the patient compresses the film and the cannula with his/her body, applying pressure to the connecting valve: this contact between the connecting valve and the part affected by the lesion not only causes pain but can worsen the conditions of the lesion.

To avoid this, the patient is often forced to stay in very uncomfortable positions for the entire duration of the drainage, which may even reach 72 hours.

Ultimately, the method of the type described entails that the polyurethane is manipulated several times: a first manipulation which serves to position the plug, a second manipulation to arrange the polyurethane compress, a further manipulation to ensure occlusion of the cavity by applying the adhesive film and finally a fourth manipulation for connecting the tube to the double layer of polyurethane and the film.

This method, in addition to being laborious and slow, also provides for the intervention of specialized personnel capable of applying the film correctly and of providing the hole for the tube.

Further, the continuous series of manipulations of the wound, in addition to being awkward and painful for patient, may also entail a greater risk of bacterial contamination.

DISCLOSURE OF THE INVENTION

The aim of the present invention is to eliminate the above-mentioned problems and drawbacks of known types of drainage device particularly for aspiration in case of therapies with aspiration, fistulas, dehiscences of surgical wounds, bedsores, traumas and similar lesions, which allows to medicate or occlude the lesion with a method which is quicker and simple to perform and requires fewer manipulations by the operator.

Within this aim, an object of the invention is to provide an aspiration device according to the invention which is comfortable for the patient and most of all does not cause pain, bleeding, rashes or risks of aggravating the conditions of the lesion.

Another object of the invention is to allow the device perfect adhesion to the skin for any type of lesion and cavity.

Another object of the invention is to provide a drainage device particularly for aspiration in case of therapies with aspiration, fistulas, dehiscences of surgical wounds, bedsores, traumas and similar lesions, with means which are easily commercially available and by using commonly used materials, so that the device is economically competitive and easy to assemble.

This aim and these and other objects, which will become better apparent hereinafter, are achieved by a drainage device according to claim 1 and, alternatively, according to claim 12.

BRIEF DESCRIPTION OF THE DRAWINGS

Further characteristics and advantages of the invention will become better apparent from the following detailed description of a preferred but not exclusive embodiment of the drainage device particularly for aspiration in case of therapies with aspiration, fistulas, dehiscences of surgical wounds, bedsores, traumas and similar lesions, illustrated by way of non-limiting example in the accompanying drawings, wherein.

WAYS OF CARRYING OUT THE INVENTION

With reference to the figures, a drainage device particularly for aspiration in case of therapies with aspiration, fistulas, dehiscences of surgical wounds, bedsores, traumas and similar lesions according to the invention is generally designated by the reference numeral 1.

One of the features of the device 1 is that it comprises an aspiration pouch 2 which is supported by a sheet-like element 5 which can be associated with a cavitary lesion 10 and is connectable to aspiration means 3 by way of a connecting element 4.

Figure 1:
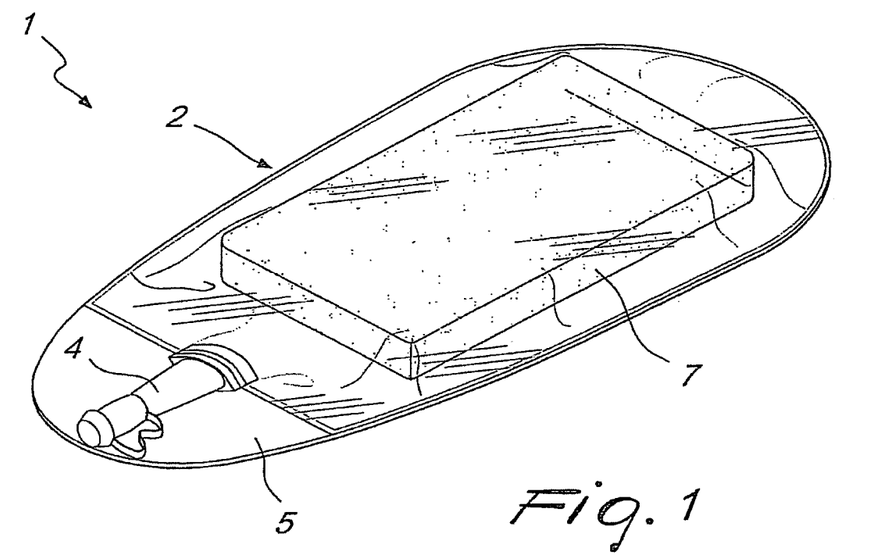
FIG. 1 is a perspective view of a drainage device according to the invention.
Figure 2:
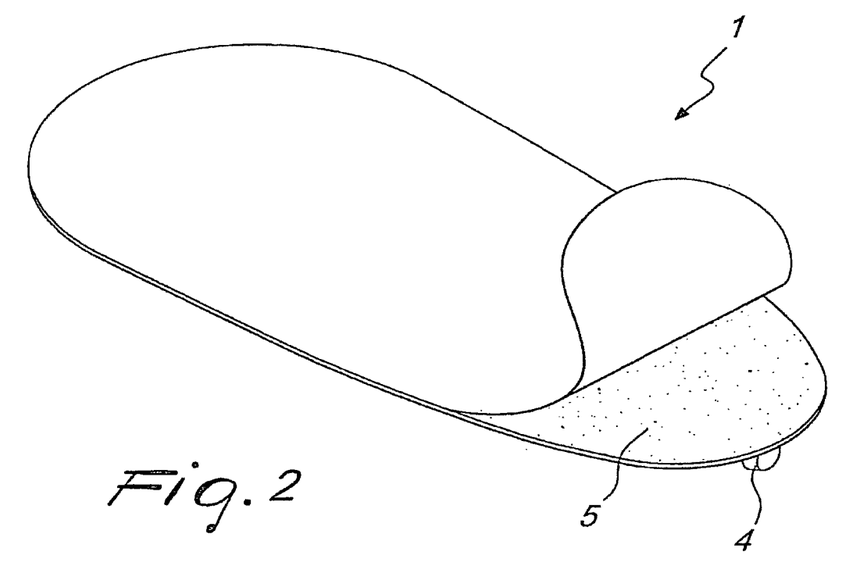
FIG. 2 is a bottom perspective view of the drainage device of FIG. 1.
Figure 3:
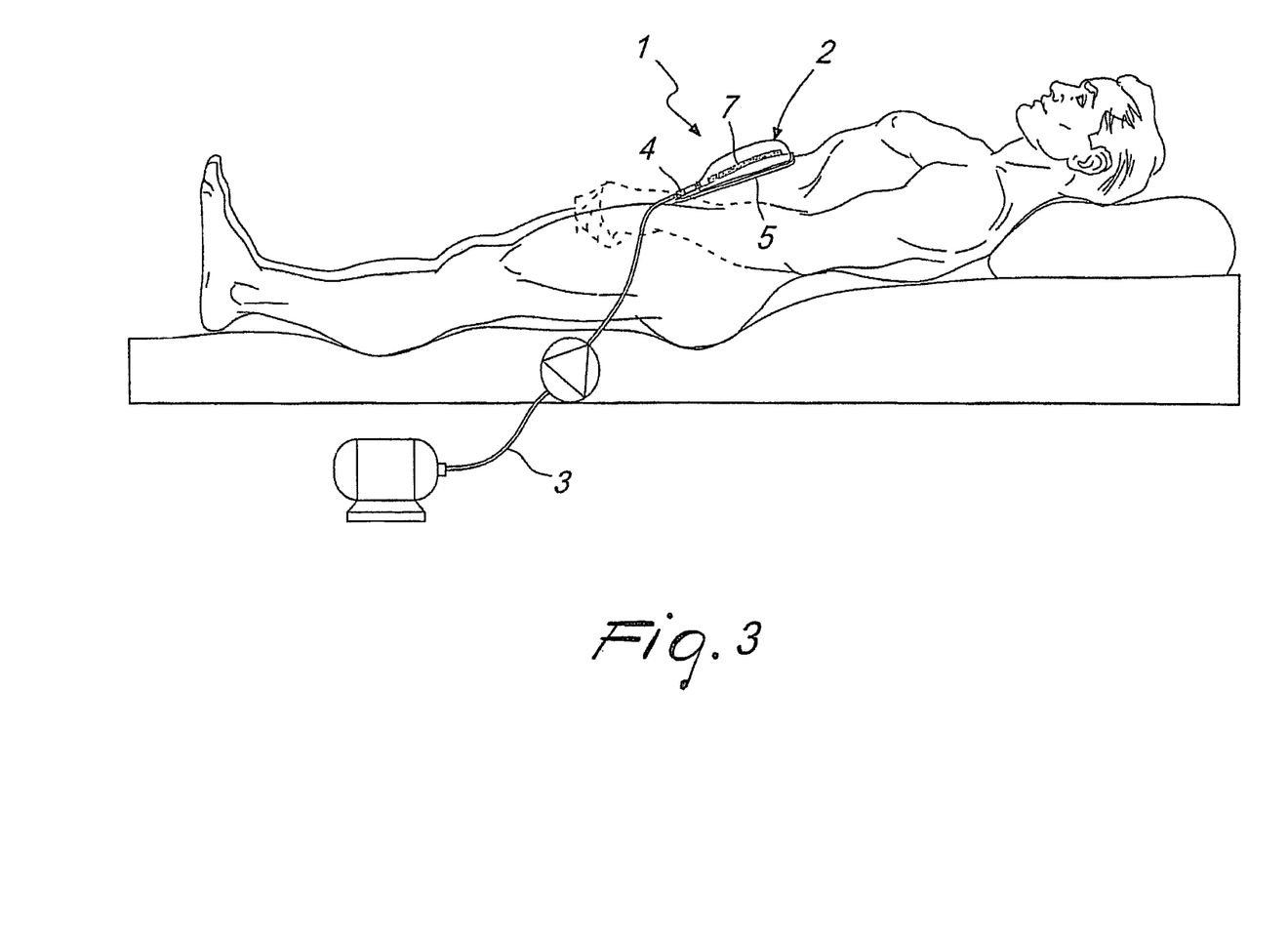
FIG. 3 is a view of the drainage device according to the invention applied to a cavitary lesion on the abdomen of a patient.
Figure 4:
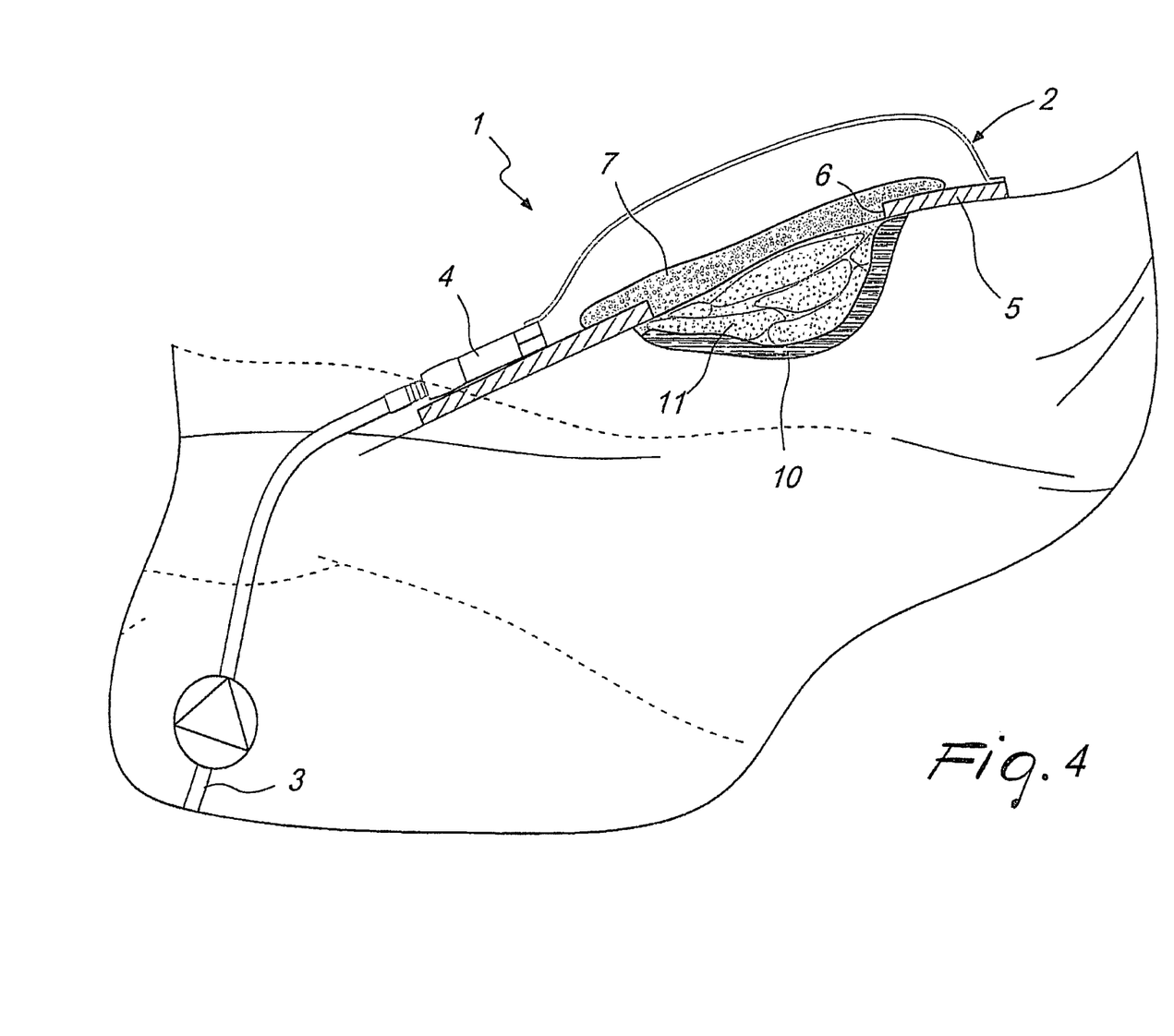
FIG. 4 is a sectional view of the drainage device according to the invention, taken along its axis of symmetry.
Figure 5:
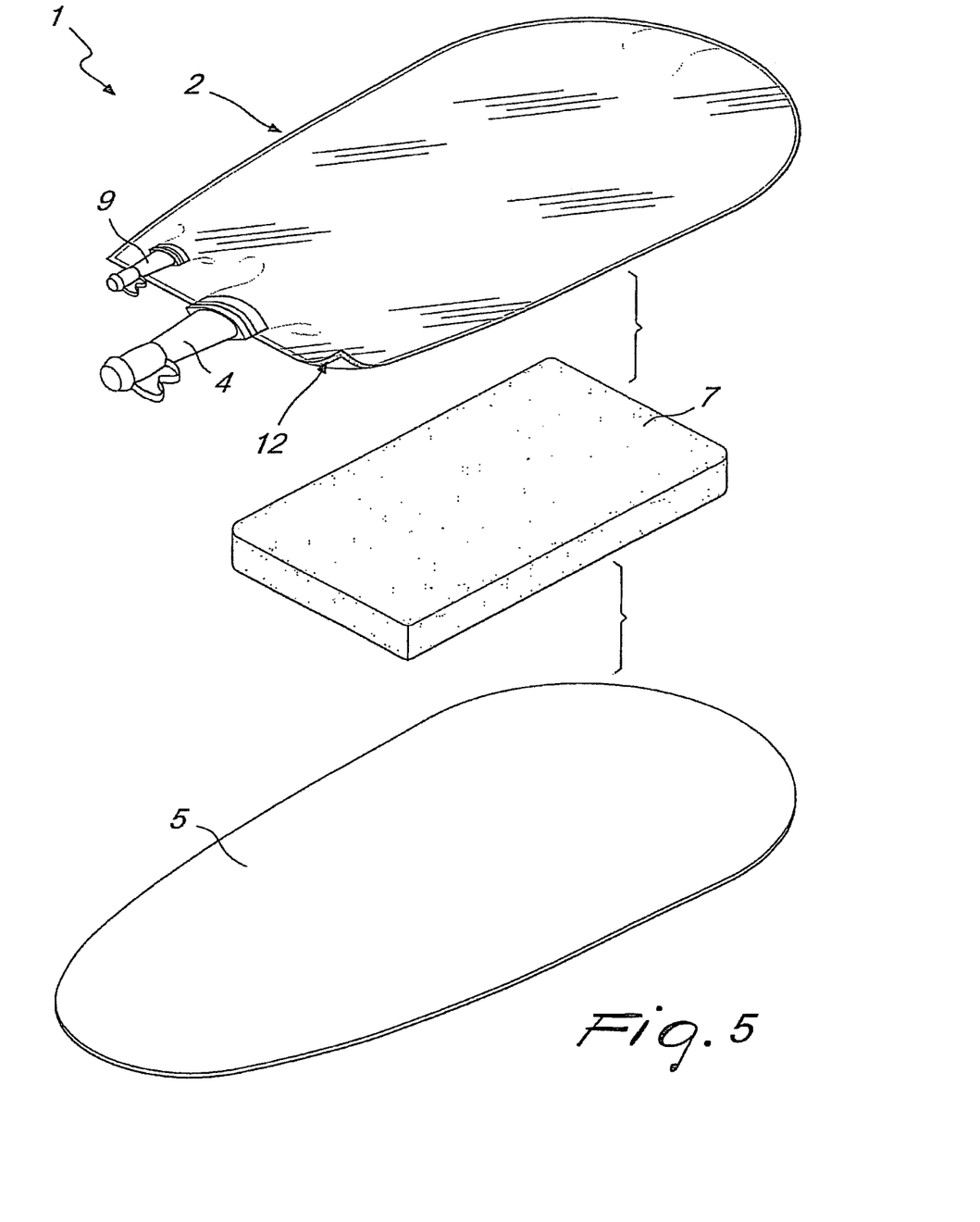
FIG. 5 is an exploded view of the drainage device according to the invention.
Figure 11:
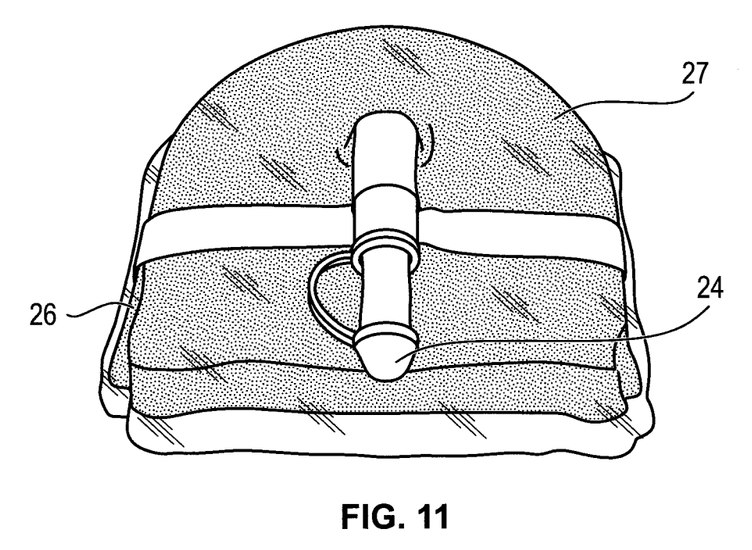
FIG. 11 is a perspective view of the front side of the drainage device according to FIG. 6; drainage layer.

Advantageously, the sheet-like element 5 supports the connecting element 4, i.e. the element 5 has such a surface as to contain both the pouch 2 and the connecting element 4. In a preferred embodiment the drainage device corresponds to FIG. 1. In another preferred embodiment the drainage device corresponds to FIG. 11. Both embodiments lead to an appropriate protection of the wound.

It is possible to provide on the sheet-like element 5 an access 6 to the lesion 10 for the pouch 2 by cutting the element 5 or by using a preformed opening appropriately.

Preferably, the sheet-like element 5 is made of a hydrocolloid material (colloidal state formed by an aqueous dispersion phase and by a dispersed phase) and has a self-adhesive surface in the embodiment described here.

By way of the essential prerogative of the hydrocolloid of being neutral with respect to the skin, this operation does not cause discomfort of any kind to the patient.

Preferably, the pouch 2 and the sheet-like element 5 can be associated with each other detachably. In the embodiment described here, in this regard a layer of adhesive material 12 has been applied to the wall of the element 5 for contact with the pouch 2.

In this manner, the operator can apply to the body of the patient the sheet-like element 5 and then associate therewith the pouch 2 without causing pain to the patient in case of errors in applying the device 1.

The connecting element 4 is constituted by a connecting valve for connecting the device 1 to the aspiration means 3 or to any reservoir.

It is possible to provide a one-way drip valve 9 connected to the aspiration pouch 2 intended to drip the disinfectant even during aspiration.

Advantageously, the pouch 2 is provided internally with a draining layer, which consists of a compress 7 made of polyurethane, usually expanded polyurethane or other material suitable for drainage, to be placed in contact with the polyurethane forming a plug 11, which is instead placed inside the lesion 10, in the part to be treated.

Further, the pouch 2 is made entirely or at least partly of optically transparent material, so as to allow visual inspection and to check that there are no leaks of blood or other types of complication.

The medication method for therapies with aspiration, fistulas, dehiscences of surgical wounds, bedsores, occlusive medications of cavitary lesions, traumas and similar lesions to be used with the drainage device 1 is as follows.

After filling the cavitary lesion with a first layer of polyurethane for the plug 11, one access 6 (preformed or cut by the operator) of the pouch 2 to the cavitary lesion 10 is provided on the sheet-like element 5.

The device 1 is then applied to the cavitary lesion 10 (as mentioned earlier, by means of the self-adhesive surface of the hydrocolloid), placing in contact a draining layer contained within the pouch 2 (for example the polyurethane compress 7) with the plug of polyurethane 11.

Once the device 1 has been applied and positioned, it is connectable to the aspiration means 3 by way of the connecting element 4, which as mentioned can be a connecting valve, for drainage.

In order to provide the access 6 on the element 5, first of all the profile of the perimeter of the cavitary lesion 10 to be occluded is traced, the tracing is cut, the cut tracing thus obtained is placed on the sheet-like element 5 to draw the contour of the access 6, and then the element 5 is cut along this contour.

Advantageously, the cutting of the contour must be undersized with respect to the perimeter of the cavitary lesion 10 by at least 2-3 mm, so that the edges of the lesion 10 are protected by the hydrocolloid. Optionally, the perimeter of the lesion 10 can be traced on the sterile package that contains the device 1.

In this manner, an access 6 is provided which can be adapted to the part to be treated, so that the device 1 can be coupled to the lesion 10 (sore, wound, fistula, et cetera) in the best possible manner, avoiding the aspiration problems mentioned earlier.

In the solution proposed here, first the sheet-like element 5, already provided with the access 6, is applied to the body of the patient, and then the pouch 2 is positioned so that the perimeter of the lesion 10 remains completely within the pouch 2.

At this point, by means of the access 6, the polyurethane compress 7 comes into contact with the plug 11 and the pouch 2 is connected, by means of the connecting element 4, to the aspiration means 3.

From what has been described above it is therefore evident that the invention achieves the proposed aim and objects, and in particular the fact is stressed that a drainage device is provided, particularly for aspiration in case of therapies with aspiration, fistulas, dehiscences of surgical wounds, bedsores, traumas and similar lesions, which allows an occlusive medication which is simple to provide and does not require expert and qualified personnel and with limited manipulations.

In particular, the provision of an aspiration pouch supported by a sheet-like element not only makes it easier to apply the device on the part of assigned personnel, which is not necessarily specialized and highly qualified, but also facilitates the connection of the device to aspiration means for draining the cavitary lesion.

Another advantage of the invention is due to the fact that the provision of the sheet-like element as a support point for the connecting element (valve) allows the patient to spend the treatment and convalescence period more comfortably, since he/she is granted a greater freedom of motion during drainage of the liquids (an operation which, as mentioned, can last even days) without the danger of the valve acting directly on the skin of the part to be treated, causing unpleasant pains and risking to worsen the lesion itself.

Another advantage of the invention is provided by the fact that filling the interior of the aspiration pouch with a compress made of expanded polyurethane or other draining material increases the draining capacity of the device, avoids additional traumas due to compression of the lesion and of the surrounding tissues, improving the effectiveness of the treatment, and that it is possible to disconnect temporarily the aspirator from the pouch without losing the draining effect of the device.

Another advantage of the device is that a one-way valve has been provided for dripping the disinfectant and can be used even during suction, when the connecting element is engaged.

Another advantage of the device is that it allows visual inspection of the drained liquids (for example if there are blood losses) by way of the provision of at least one wall of the pouch by using optically transparent material; this allows to intervene promptly in case of any problems.

Further, by way of the possibility to cut out an access from the tracing of the perimeter of the cavity, in particular by undersizing the provided hole, not only is a perfect adhesion provided between the skin and the pouch, avoiding air infiltrations during drainage, determining extreme asepsis and facilitating aspiration by partial vacuum, but a totally occlusive medication is also insured without causing problems in terms of bleeding and skin irritations of the lips of the skin of the lesion.

Figure 17:
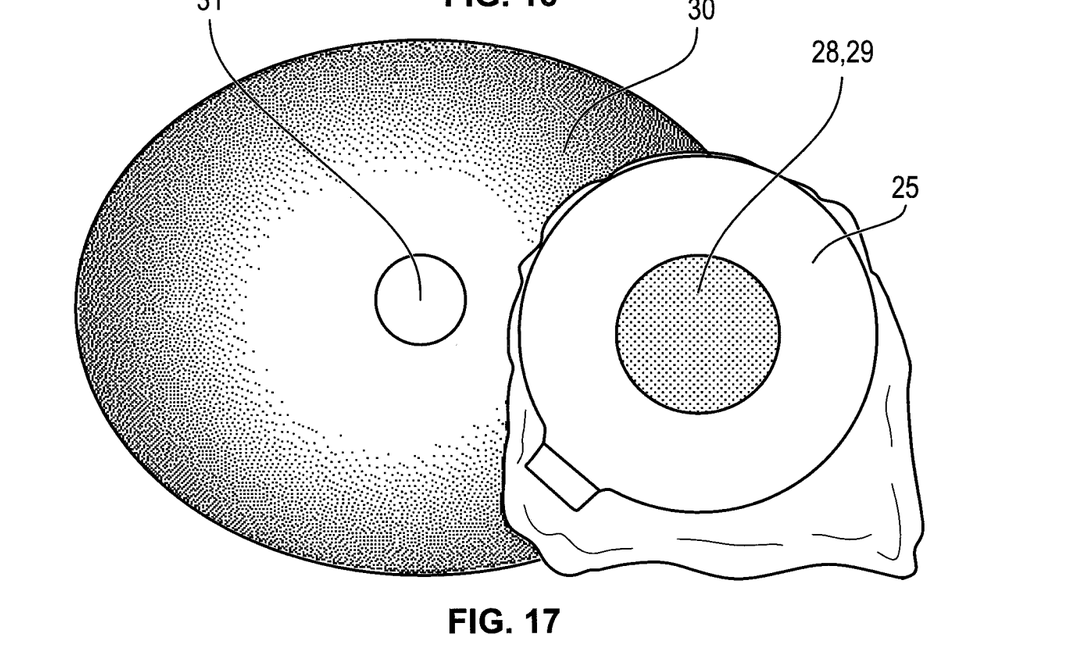
FIG. 17 shows the elements according to FIG. 16 taken apart.

Another advantage of the invention is that the pouch and the sheet-like element can be associated detachably (see for example FIG. 17). In this manner, in addition to avoiding pain to the patient if the less than expert operator makes mistakes in positioning, facilitating its application, it is advantageously possible to sterilize the pouch and the hydrocolloid in order to be able to reuse them: the pouch in fact normally requires a gas sterilization, while the hydrocolloid must be sterilized with cobalt.

Moreover, the provision of the sheet-like element with materials commonly used in this medical field, as well as the use of a technology which is simple and inexpensive to install and use the aspiration device, makes the invention highly competitive with respect to the background art and equally effective.

In practice it has been found that the device according to the invention thus described allows to treat the patient affected by lesions such as stomas, fistulas, dehiscences from surgical wounds, bedsores and the like, or needing medications, particularly occlusive medications, even without hospitalization or the aid of qualified and highly specialized personnel, making the step of treating the patient more comfortable.

Figure 8:
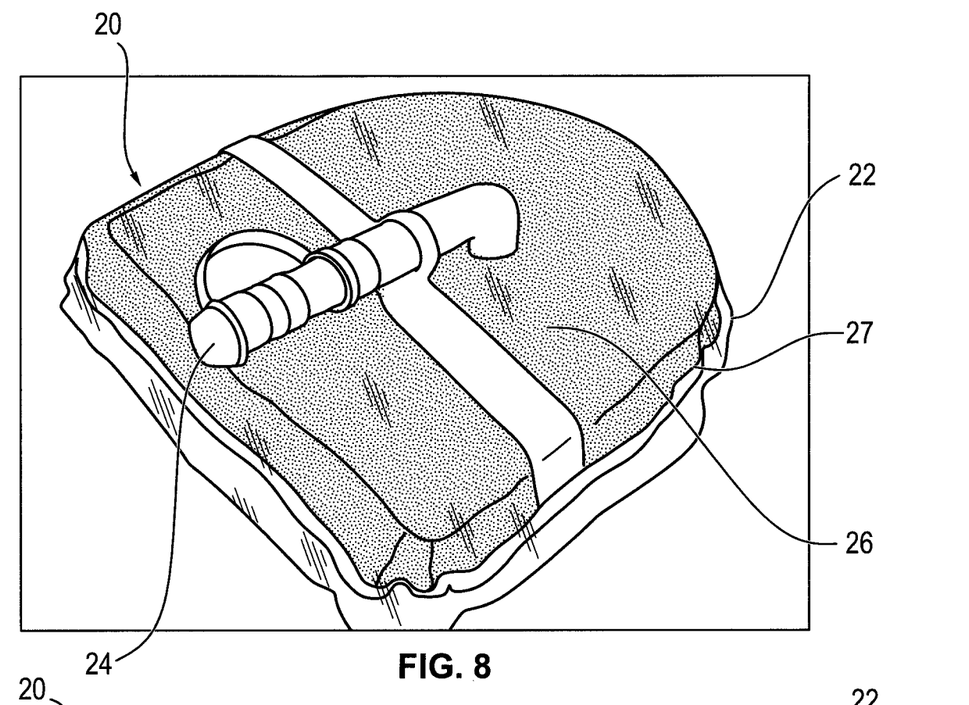
FIG. 8 is a perspective view of the drainage device according to FIG. 6 seen from the top.
Figure 9:
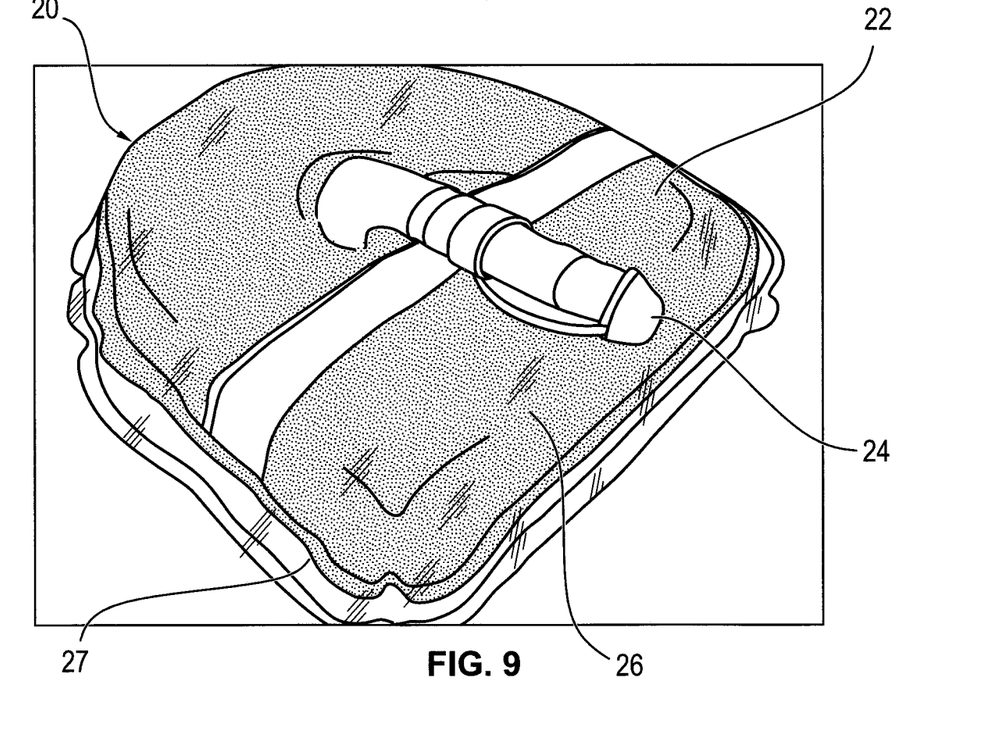
FIG. 9 is a perspective view of the drainage device according to FIG. 6 seen from the top from a different angle.
Figure 14:
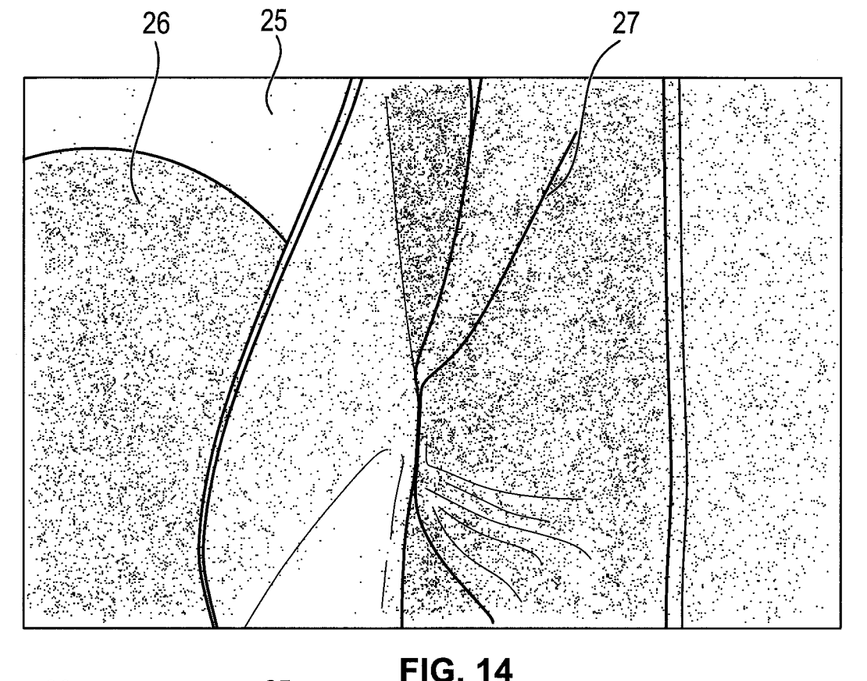
FIG. 14 shows a detail of the drainage device according to FIG. 6 in the area of the connection between the sheet-like element and the foil.
Figure 15:
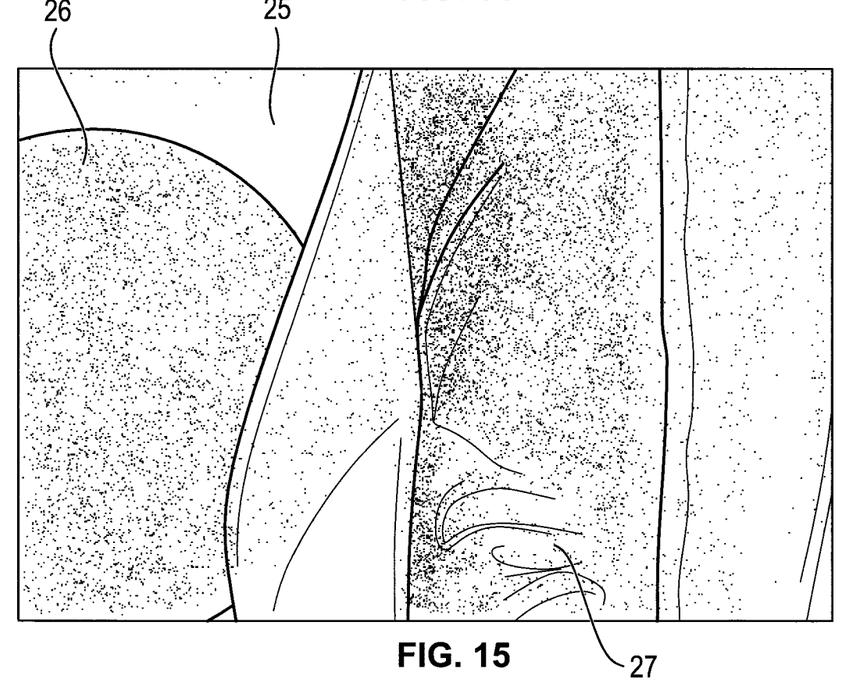
FIG. 15 shows a detail of the drainage device according to FIG. 6 in the area of the connection between the sheet-like element and the foil.

In the following, a further embodiment of the invention is described in connection with FIGS. 6 to 17. The further embodiment concerns a drainage device 20 which comprises an aspiration pouch 22 supported by a sheet-like element 25. To this end, the sheet-like element overlaps at least partially, in particular completely the aspiration pouch 22 and is arranged on the bottom side of the aspiration pouch. Thus, the sheet-like element 25 is adapted to be associated with a cavitary lesion (not shown) and forms a support for the aspiration pouch 22 arranged on top of the sheet-like element 25. In other words, the sheet-like element 25 is arranged in use between the cavitary lesion and the aspiration pouch 22. As shown in FIGS. 8, 9 the aspiration pouch 22 is connectable to aspiration means (not shown) or to a drainage pouch (not shown) by way of the connecting element 24 which can be for example a valve. As evident from FIGS. 6, 7 the aspiration pouch comprises at least one draining layer 26 which is surrounded by a gas- and fluid tight foil 27. The foil 27 encloses the draining layer 26 on the top of the draining layer 26 and all side faces of the draining layer 26 (FIGS. 8, 9, 10, 11). The foil 27 further encloses the draining layer 26 on the bottom of the draining layer 26 and extends radially inwardly so as to cover at least partially the bottom of the draining layer 26 (FIGS. 14, 15).

The foil 27 is made of a gas- and fluid tight material which is adapted to fulfil the function of a gas- and fluid barrier that allows a controlled aspiration of the fluids coming from the cavitary lesion.

The foil 27 forms a first opening 28 as shown in FIGS. 6, 7 and FIGS. 13 to 14. Through the first opening 28 fluids can be drawn off out of the cavitary lesion. Thus, the first opening 28 is adapted to be associated with the cavitary lesion.

The sheet-like element 25 is provided on the same side of the draining layer 26 as the first opening 28 in the foil 27. The sheet-like element 25 reinforces the first opening 28. To this end, the sheet-like element 25 comprises a second opening 29 which matches with the first opening 28. It is also possible that the first and second openings partially overlap as long as an access is formed which allows a fluid connection between the cavitary lesion and the draining layer 26. The sheet-like element 25 is gas- and fluid tightly connected with the foil 27. Therefore, the sheet-like element 25 and the foil 27 together form an gas- and fluid tight pouch or envelope which contains the draining layer 26. The access to the draining layer 26 is achieved by the first and second openings 28, 29 formed in the sheet-like element 25 and the foil 27.

Figure 13:
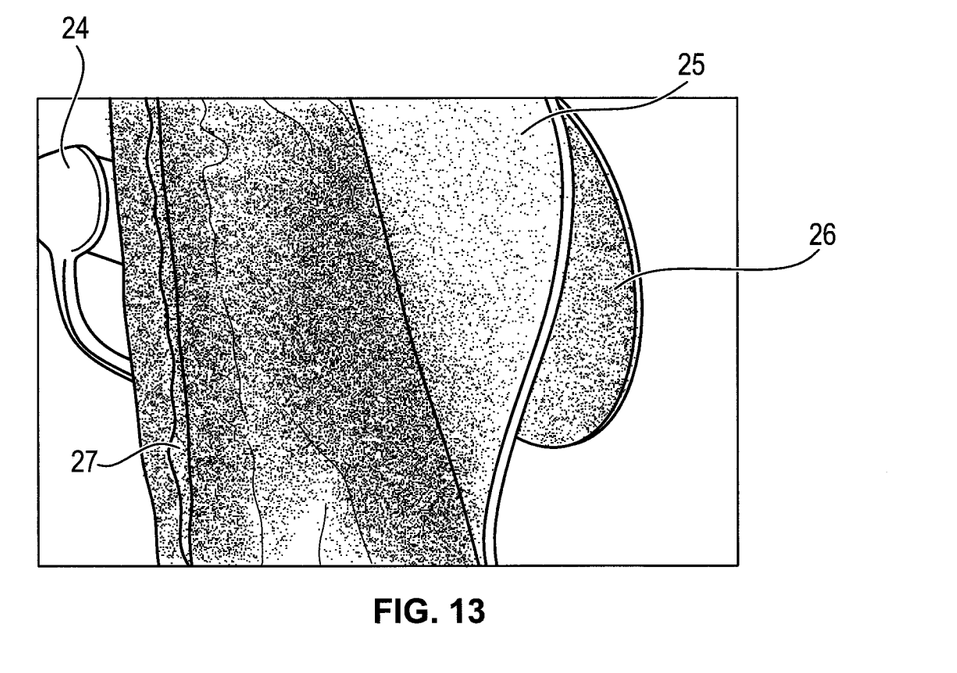
FIG. 13 is a perspective view of a detail of the drainage device according to FIG. 6 showing the connection between the sheet-like element and the foil.

The fluid- and gas tight connection between the sheet-like element 25 and the foil 27 is illustrated in FIGS. 13 to 14. There it can be taken that an annular edge of the sheet-like element 25 surrounding the first and second openings 28, 29 is connected with the foil 27 for example by means of an adhesive. The width of the edge connecting the sheet-like element 25 and the foil 27 can be freely chosen by a person skilled in the art as long as the tightening function is given. Other means of connection are possible, for example by means of welding.

Figure 6:
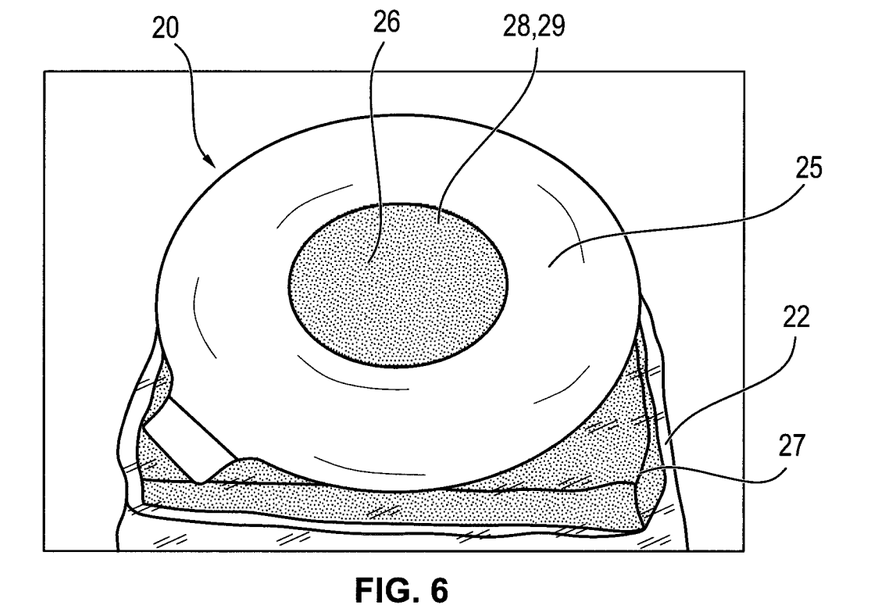
FIG. 6 is a perspective view of the drainage device according to a further embodiment of the invention seen from the bottom.
Figure 7:
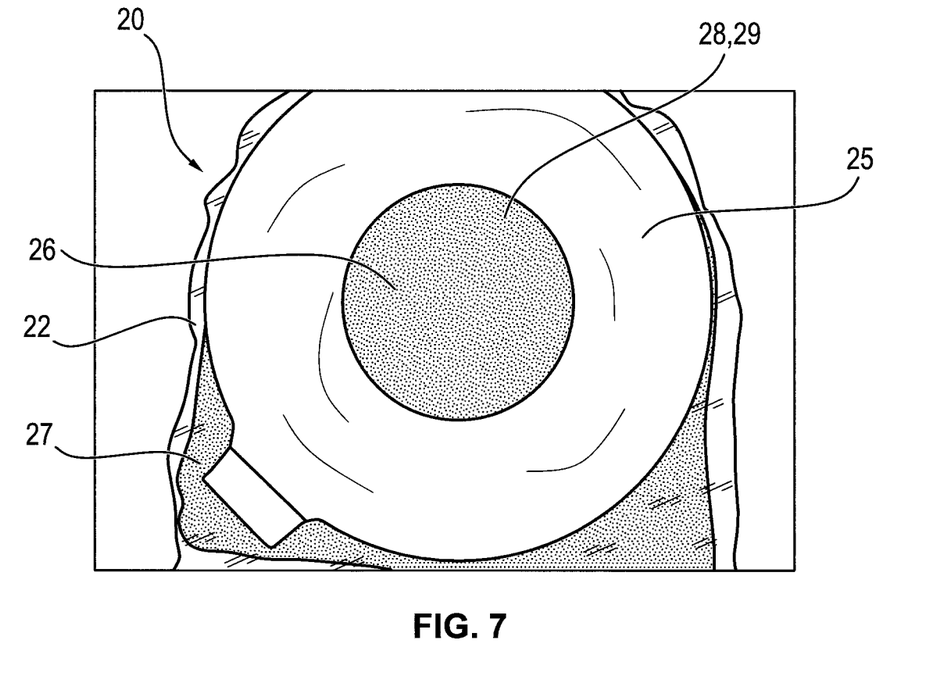
FIG. 7 is a perspective view of the drainage device according to FIG. 6 seen from a different angle.
Figure 10:
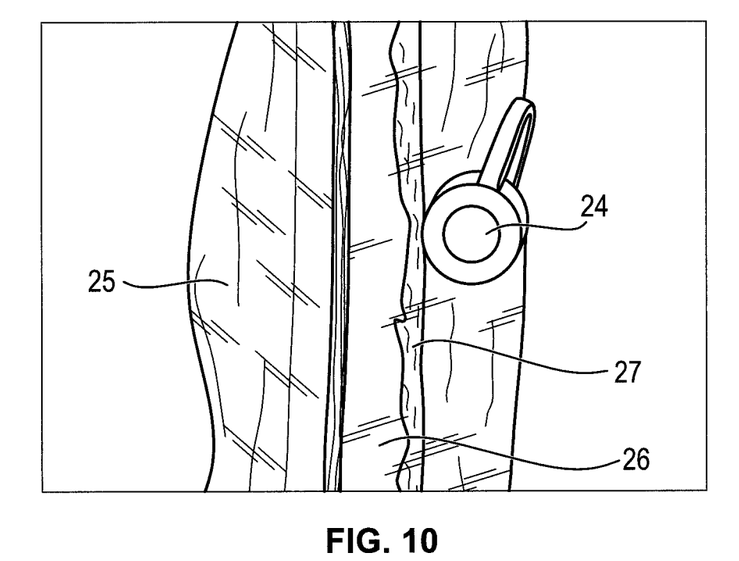
FIG. 10 is a front view of the drainage device according to FIG. 6.

As best seen in FIGS. 6,7 the sheet-like element 25 is an annular element. The annular element overlaps or can overlap with the draining layer 26 so as to give support to the same in use. Other forms as the sheet-like element are possible as long as the sheet-like element overlaps with the draining layer to support the same and to give access to the draining layer contained in the aspiration pouch 22. The sheet-like element 25 can be connected to a hydrocolloid plate (FIGS. 16, 17) either in the form of an integral element or upon use. As illustrated in FIG. 10, the sheet-like element 25 and the connecting element 24 are provided on different, in particular on opposing sides of the aspiration pouch 22. In particular, the connecting element 24 is provided on the top of the draining layer in such a manner that in use the draining layer 26 is arranged between the cavitary lesion and the connecting element 24 to protect the cavitary lesion from a contact with the connecting element 24. The connecting element 24 is connected with the foil 27 approximately on the same level as the openings 28, 29 which allows for an efficient aspiration of the fluids out of the cavitary lesion.

Figure 12:
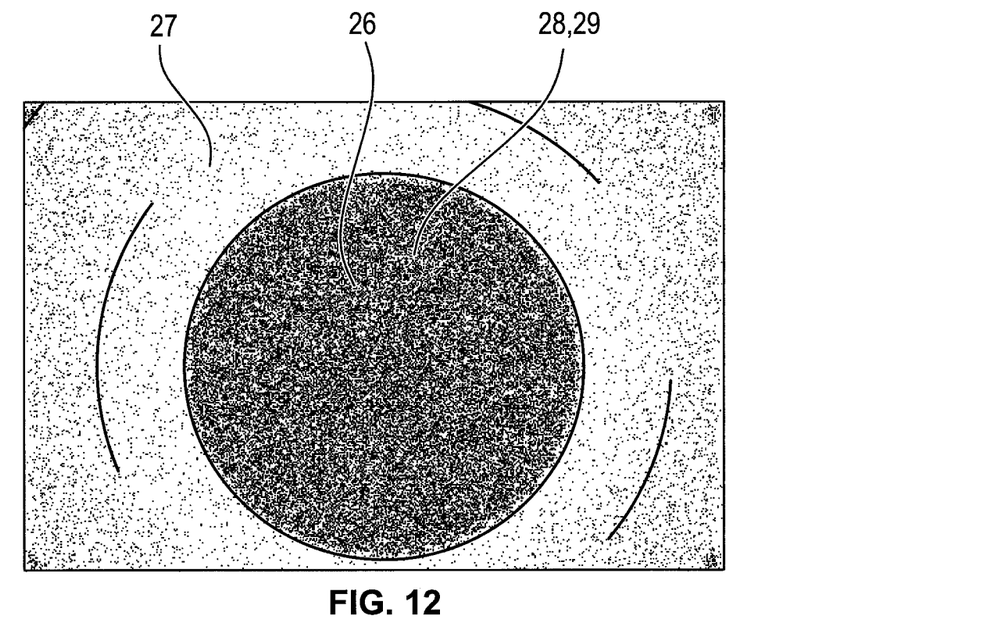

As seen in FIG. 12, the draining layer 26 is formed of a porous material that is able to absorb fluid out of the cavitary lesion.

Figure 16:
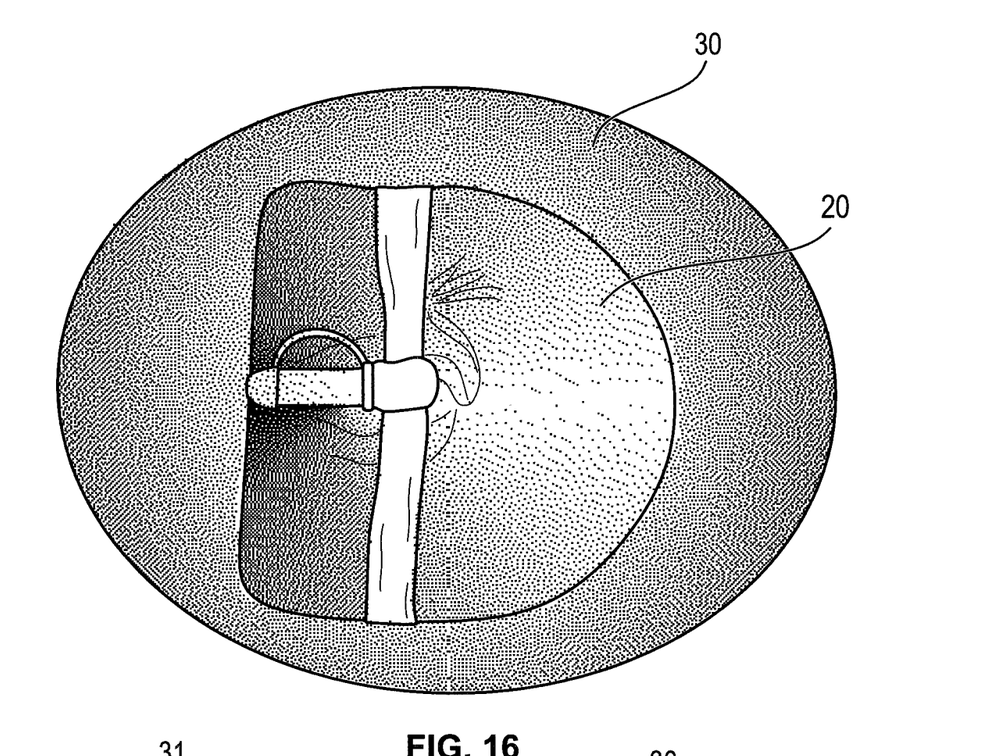
FIG. 16 shows a perspective view of the drainage device according to FIG. 6 combined with a second sheet like element.

According to a further embodiment shown in FIGS. 16, 17 the aspiration pouch can be combined with a further sheet-like element 30 which is provided with a third opening 31. In use, the third opening 31 matches or is aligned with the first and second openings 28, 29 to give access to the draining layer 26. The outer contour of the further sheet-like element 30 is larger than the outer contour of the aspiration pouch 20. Moreover, the third opening 31 is smaller than the first and second openings 28, 29. These features facilitate the positioning of the aspiration pouch 20 on the cavitary lesion and enhance the secure handling such that the draining layer 26 interacts with the cavitary lesion.

The embodiment of the invention according to FIGS. 6 to 17 has the advantage that the draining layer and the aspiration pouch form an integral part owing to the gas- and fluid tight foil 27 which encapsulates the draining layer 26. The access opening 28 in the foil 27 is reinforced by the sheet-like element 25 which, moreover, has the function to support the aspiration pouch 20. The integral structure of the aspiration pouch 20 allows for a save and easy handling of the aspiration pouch 20. The save and easy handling is further improved if the aspiration pouch is used together with the further sheet-like element 30 which facilitates the positioning of the device.

The device, which is also called WoundBag is an external bandage. It is applied after the wound or the cavitary lesion is completely filled with a bandage material which can be freely chosen by the user.

The WoundBag-system can be comprised of one single component (FIGS. 6 to 15) or of two separate components (FIG. 16, 17) or of even more components. The system with one component comprises a hydrocolloid basis or plate on which the WoundBag filled with the drainage layer 26, for example made of polyurethane, is attached. The system comprising two components consists of a hydrocolloid basis and the filled WoundBag which are handled separately and brought together only upon application to the lesion.

The one part as well as the two part system consist of prefabricated parts and are applied to achieve an occlusive bandage.

The WoundBag is provided with a fixedly attached valve. The valve can be used as follows:

The valve can be joined with a pouch by means of a connecting tube, to achieve a closed drainage. The valve can be connected with a sucking device by means of a connecting tube. The valve can be simply closed.

The WoundBag filled with the polyurethane layer or any other absorbing layer can be provided with two valves or even with more than two valves. The second valve is connected with a nelaton or a drainage means to achieve a continuous lavage. In this case, the first valve can be connected to a receiving pouch by means of a tube, to achieve a closed drainage. Alternatively the first valve can be connected to a sucking device.

The hydrocolloid plate of the WoundBag system both in the one part and in the two part variation is used to protect the edges of the lesion and the area surrounding the lesion: Moreover, the hydrocolloid plate has the function to close the lesion. The pouch contains a polyurethane layer or any other absorbing material layer and functions as an external bandage. The WoundBag system does not require an adhesive film to achieve the occlusion of the lesion. The embodiment according to which the WoundBag comprises one or two fixedly attached valves has the advantage that no additional connector is required to carry out a potential therapy either by means of a closed drainage or by means of a sucking device.

All features of the embodiment according to FIGS. 6 to 17 are disclosed in connection with the features of the embodiment according to FIGS. 1 to 5.

The invention thus conceived is susceptible of numerous modifications and variations, all of which are within the scope of the appended claims.

All the details may further be replaced with other technically equivalent elements.

In practice, the materials used, as well as the dimensions, may be any according to requirements.

The disclosures in Italian Patent Application No. AR2008A000022 from which this application claims priority are incorporated herein by reference.

Where technical features mentioned in any claim are followed by reference signs, those reference signs have been included for the sole purpose of increasing the intelligibility of the claims and accordingly, such reference signs do not have any limiting effect on the interpretation of each element identified by way of example by such reference signs.

The invention claimed is:

1. A drainage device comprising an aspiration pouch supported by a sheet comprising a hydrocolloid substance, the sheet being arranged on a bottom side of the aspiration pouch and overlapping at least partially the aspiration pouch,
   wherein the sheet includes an opening that provides an access to a cavitary lesion,
   wherein the aspiration pouch defines an interior volume comprising at least one draining layer,
   wherein said at least one draining layer comprises at least one polyurethane compress,
   wherein the aspiration pouch is connectable to aspiration means by way of a connecting valve which is provided outside the aspiration pouch and on the top of the at least one draining layer; and
   wherein the aspiration pouch comprises a gas- and fluid tight foil that partially encloses the draining layer and extends radially inwardly so as to partially cover the bottom of the draining layer.

2. The drainage device according to claim 1, wherein said sheet has a surface which can be associated with the skin of patient by way of adhesive means.

3. The drainage device of claim 1, wherein the at least one draining layer consists of one polyurethane compress.

4. The drainage device of claim 1, wherein the interior volume consists of the at least one draining layer and gas.

5. The drainage device according to claim 1, wherein the sheet is detachably associated with said aspiration pouch.

6. The drainage device according to claim 5, wherein said aspiration pouch comprises at least one portion of optically transparent material.

7. The set of claim 6, wherein the aspiration pouch comprises at least one portion of optically transparent material.

8. The drainage device according to claim 5, further comprising a one-way drip valve connected to said aspiration pouch.

9. A set for assembling a drainage device, including a sheet comprising a hydrocolloid; and an aspiration pouch defining an interior volume consisting essentially of at least one polyurethane compress, wherein the sheet and the aspiration pouch can be associated with each other detachably, the set further comprising a connecting valve located outside the aspiration pouch and above the polyurethane compress, wherein the aspiration pouch comprises a gas- and fluid-tight foil that extends radially inwardly to partially cover the bottom of the polyurethane compress.

10. The set of claim 9, wherein the at least one polyurethane compress consists of one polyurethane compress.

11. The drainage device of claim 9, wherein the at least one draining layer consists of one polyurethane compress.

12. The set of claim 9, wherein the interior volume consists of at the at least one draining layer and gas.

13. The set of claim 12, wherein the at least one draining layer consists of a polyurethane compress.

14. The set of claim 9, further comprising a one-way drip valve connected to the aspiration pouch.

15. A method for assembling the drainage device according to claim 1 on a lesion comprising the following steps:
applying the sheet to the lesion such as to protect the edges of the lesion and the lesion in accessible via the opening;
covering the opening with the aspiration pouch; and
connecting the aspiration pouch with the aspiration means by way of the connecting valve.

16. The method of claim 15, wherein the at least one draining layer consists of one polyurethane compress.

17. The method of claim 15, wherein the interior volume consists of the at least one draining layer and gas.

18. The method of claim 17, wherein the at least one draining layer consists of one polyurethane compress.

19. The method of claim 15, wherein the drainage device further comprises a one-way drip valve connected to the aspiration pouch.

* * * * *